US011684470B2

(12) United States Patent
Dockhorn et al.

(10) Patent No.: US 11,684,470 B2
(45) Date of Patent: Jun. 27, 2023

(54) INJECTOR, IN PARTICULAR DUAL FUNCTION INJECTOR AND/OR INJECTOR WITH STOP ELEMENT

(71) Applicant: MEDICEL AG, Altenrhein (CH)

(72) Inventors: Volker Dockhorn, Altenrhein (CH); Reto Germann, Altenrhein (CH)

(73) Assignee: MEDICEL AG, Altenrhein (CH)

( * ) Notice: Subject to any disclaimer, the term of this patent is extended or adjusted under 35 U.S.C. 154(b) by 429 days.

(21) Appl. No.: 17/047,058

(22) PCT Filed: Apr. 10, 2019

(86) PCT No.: PCT/CH2019/050006
§ 371 (c)(1),
(2) Date: Oct. 12, 2020

(87) PCT Pub. No.: WO2019/195951
PCT Pub. Date: Oct. 17, 2019

(65) Prior Publication Data

US 2021/0154004 A1 May 27, 2021

(30) Foreign Application Priority Data

Apr. 12, 2018 (CH) .................................... 00467/18

(51) Int. Cl.
*A61F 2/16* (2006.01)

(52) U.S. Cl.
CPC .................................. *A61F 2/1672* (2013.01)

(58) Field of Classification Search
CPC .......... A61F 2/16; A61F 2/148; A61F 2/1662; A61F 2/1672
See application file for complete search history.

(56) References Cited

U.S. PATENT DOCUMENTS 4,810,249 A 3/1989 Haber et al.
2008/0097461 A1* 4/2008 Boukhny ............. A61F 2/1678 606/107

(Continued)

FOREIGN PATENT DOCUMENTS

| | | |
|---|---|---|
| GB | 2501109 A | 10/2013 |
| KR | 101648817 B1 | 8/2016 |
| WO | 2011126144 A1 | 10/2011 |

OTHER PUBLICATIONS

PCT International Preliminary Report on Patentability for PCT/CH2019/050006, dated Oct. 13, 2020, 9 pages.

(Continued)

*Primary Examiner* — Vi X Nguyen
(74) *Attorney, Agent, or Firm* — Morriss O'Bryant, Compagni Cannon, PLLC

(57) ABSTRACT

An injector for ejecting an intraocular lens for injecting the latter into an eye or for implanting a corneal endothelial tissue, including an elongate injector body which has a piston rod passage and in which an injector piston rod having a screw thread is guided in a longitudinally displaceable manner. The injector is provided with two operating modes for the displacement of the injector piston rod and is able to be switched between the modes. The first operating mode defines an ejection operation and the second operating mode defines a screwing operation. The injector body has at least one retractable and deployable wing grip, wherein the operating mode is set to ejection operation by the deployed position and the operating mode is set to screwing operation by the retracted position. The injector piston rod includes a stop element.

25 Claims, 11 Drawing Sheets

11
19
22
26
28
17
33
24
13
25
27
16

(56) References Cited

U.S. PATENT DOCUMENTS

| | | | | |
|---|---|---|---|---|
| 2009/0112223 | A1* | 4/2009 | Downer ................ | A61F 2/1667 606/107 |
| 2014/0257317 | A1 | 9/2014 | Safabash | |

OTHER PUBLICATIONS

PCT International Search Report for PCT/CH2019/050006, dated Aug. 9, 2019, 3 pages.
PCT Written Opinion for PCT/CH2019/050006, dated Aug. 9, 2019, 8 pages.

* cited by examiner

INJECTOR, IN PARTICULAR DUAL FUNCTION INJECTOR AND/OR INJECTOR WITH STOP ELEMENT

CROSS-REFERENCE TO RELATED APPLICATIONS

This application is a national phase entry under 35 U.S.C. § 371 of PCT/CH2019/050006 filed Apr. 10, 2019, which claims priority to Swiss Patent Application No. 00467/18 filed Apr. 12, 2018, the entirety of each of which is incorporated by this reference.

TECHNICAL FIELD OF THE INVENTION

The field of the invention comprises an injector, in particular an injector for injecting an intraocular lens (IOL) into an eye or for implanting a corneal endothelial tissue in an eye.

BACKGROUND OF THE INVENTION

The injectors customary in the past for inserting intraocular lenses (IOL) are either designed in syringe form, which can be operated with one hand, or are designed with a screw thread, which are usually operated with two hands. Depending on which technique a surgeon has learned or prefers, he will choose an ejection injector or a screw injector.

In addition to the aforementioned ejection injectors and screw injectors, there are also systems that combine both functionalities (i.e., that of an ejection injector and that of a screw injector), i.e., they are dual, e.g., the IOL injector DualTeem provided by OPHTEC BV. Dual systems are also known in the field of syringes, e.g., in U.S. Pat. No. 4,810,249. Dual-functional systems have the advantage that it is sufficient to give the surgeon only one type of injector or one type of syringe (or to keep it in stock), because it is up to the surgeon to decide in which functionality he will use it. Especially with IOL systems in which the IOL is already preloaded in the injector, storage and procurement costs for lens manufacturers and end users can be almost halved when using a system with an optional eject/screw mechanism, since only one system must be held in stock. The previously available IOL injectors with dual functions, however, have a significant shortcoming. This shortcoming is that the housing design and in particular the grip plate required for the ejection function, which is used in ejection injectors, is extremely obstructive when using the injector in screwing function, since the injector is used with two hands in screwing function, unlike in ejection function and the grip plate is in the way in doing so.

Another disadvantage of injectors, regardless of whether they are ejection injectors or screw injectors, is the variability of the piston end point in relation to the nozzle outlet (despite the constant construction). If an elastic plunger, e.g., a silicone plunger, is used on the piston rod, a particularly high variability is to be expected. This is due to the fact, e.g., that the length of the piston rod is not always exactly the same. In particular, when using an elastic plunger (such as, e.g., a silicone plunger) on the piston tip, it is not possible to determine the total length of the piston exactly. Depending on the lens material, lens geometry, dioptre, viscoelastic solution, temperature, feed speed, etc. used, the elastic plunger is compressed (i.e., shortened) or elongated (i.e., lengthened) to a greater or lesser extent, which, depending on the conditions, leads to a different overall length of the piston. This is critical because, on the one hand, the plunger must always reach the end of the injector nozzle so that the lens can always be pushed out of the injector nozzle in any case, on the other hand, the plunger should not be pushed out of the injector nozzle because the plunger which has been compressed in the injector nozzle expands to such an extent that it can no longer be retracted into the injector nozzle. When pulling out of the eye, the incision can tear open or the eye can be injured by the protruding, expanded silicone plunger.

Furthermore, with both types of injectors, regardless of whether they are ejection injectors or screw injectors, it is difficult in practice to advance the piston rod safely and infallibly in one or more consecutive predetermined feed stages. In particular, it is difficult to configure the injector so that the feed stage ends in one or each of the feed stages ends in one defined feed position each, which simultaneously serves as the starting position from which the actual injection or, if necessary, the next feed stage can follow. In particular, each feed position should define a precise piston rod feed to which the piston rod tip (i.e., the front end of the piston rod), in particular a plunger attached to the front end of the piston rod, can be precisely set. Such a feed position may be necessary, for example, to apply the so-called haptics of the IOL to the optics in a defined manner or to block the IOL from slipping out of the loading chamber with the silicone plunger.

There are IOL systems with a snapper (spring part), which prevents the piston tip or the plunger sitting on it from falling out of the injector housing. Examples are the commercially available injector systems VISCOJECT™, NAVIJECT™ and ACCUJECT™ from Medicel AG. An additional function of this catch is to secure a second feed position of the piston. For this purpose, the snapper jumps out of a first hole in the injector housing when it is first pushed forward, pushes forward and locks in place in a second hole in the injector housing. This second snap can be felt and/or connected with a small "click". In spite of this, this second piston position is often ignored or overlooked in practice and therefore passed over. The problem is that the resistance generated by the snap would have to be made so strong that an unintentional passing over could be avoided. However, such a strong snap-in or such a strong resistance would also lead to the fact that pushing out of this feed position would generate a sudden movement as the injector continues to advance (namely at the moment when the resistance is overcome), so that the IOL is moved forward over a larger area in an uncontrolled and sudden manner However, this contradicts the requirement that an IOL must be advanced in a controlled manner at all times.

The problems mentioned with regard to the variability of the piston end point and the avoidance of passing over the feed position also occur with injectors with dual functions.

Advantages

The present invention provides an alternative injector. In particular, it is an aim to develop an injector which solves all of the problems mentioned or as many as possible.

In particular, an injector is to be developed which, taking into account the above requirements, can be used either as an ejection or screw injector (i.e., push or screw injector). In particular, structures that are relevant for an ejection function should not be a hindrance when using the injector as a screw injector and, conversely, structures that are relevant for a screwing function should not be a hindrance when using the injector as an ejection injector.

Another aim is to develop such a system that allows repeated switching from ejection to screwing operation and vice versa. This means that a reversible solution should be found. In addition, the system should offer sufficient stability to be able to inject an interocular lens into an eye and at the same time also be inexpensive.

The aim is also to minimize the variability of the piston end point in relation to the nozzle outlet, especially when using an elastic plunger on the piston rod. This solution should be applicable for ejection injectors and screw injectors and in particular also dual injectors, i.e., injectors with ejection and screwing function.

The aim is to improve the setting of the piston on feed stages, in particular to improve it so that predetermined feed stages can be sensed (e.g., visually, auditorily and/or tactilely) infallibly by the surgeon and the piston can be precisely set without the lens being moved in an uncontrolled manner during further feed from a feed position. This is particularly important for feed positions from which the piston rod tip is to come into contact with the lens with the next feed step or in which the piston rod is already in contact with the lens.

SUMMARY OF THE INVENTION

The invention further relates to an injector (e.g., an injector for ejecting an intraocular lens for the purpose of injecting it into an eye or an injector for implanting a corneal endothelial tissue) comprising an elongate injector body which has a piston rod passage and in which an injector piston rod having a screw thread is guided in a longitudinally displaceable manner (in the axial direction of the injector piston rod), wherein the injector is provided with two operating modes for the displacement of the injector piston rod and is able to be switched between said modes, wherein the first operating mode defines an ejection operation and the second operating mode defines a screwing operation and wherein the injector is characterized in that the injector body has at least one retractable and deployable (or pivotable in and out) wing or wing grip, wherein the operating mode is set to ejection operation by the deployed position and the operating mode is set to screwing operation by the retracted position. This means that the injector can be used as an ejection injector or as a screw injector. The at least one wing or wing grip is positioned along the length of the injector body.

If the wing grip is deployed, this means that the wing with its grip area protrudes from the injector body in a graspable position and can be gripped from the front (i.e., from the nozzle side of the injector), for example to use a three-finger grip with one hand (i.e., one finger each on a wing grip and a third finger (or the thumb) at the rear end of the piston rod) to push the injector piston rod against the wing grip and push towards the nozzle.

In the deployed position, the wing grips protrude like a wing from the injector body. In the deployed position, the wing grips are expediently blocked against further deployment or retraction backwards, i.e., towards the proximal end of the injector. Grip areas on the wing grip are expediently positioned on that side of the wing grip which is facing the injector nozzle when the wing grip is deployed. The wing grips are expediently designed in such a way that in the deployed position the grip areas thereof serve as counter-pressure surfaces for a pressure surface on the proximal end of the injector piston rod. In particular, the wing grips are designed in such a way that they, in the deployed position, i.e., in the ejection function position, withstand at least a compressive force on the grip areas which corresponds to the ejection force applied to the proximal end of the injector piston rod. In particular, the deployed wing grips should withstand a force of at least 10 Newton, at least 20 N or at least 30 N.

The at least one retractable and deployable wing grip is expediently deployable from the front with respect to the injector body and is retractable again towards the front. The at least one wing grip is designed in particular such that it can be retracted towards the front, that is to say by means of a folding movement towards the injector nozzle, and can be deployed towards the back, that is to say by means of a folding movement towards the proximal end of the injector.

If the wing grip is retracted, this means that the wing with its grip area rests on the injector body along its length and is recessed into the side wall of the injector so that the injector body outer wall and the retracted wing form a relatively straight or homogeneous surface so that the injector body can be held with a first hand without obstruction (e.g., like a pen), for example to screw the injector piston rod towards the nozzle with the second hand.

The injector is advantageously characterized in that, depending on the position of the at least one wing grip, the injector functions as an ejection injector or as a screw injector (dual injection function). In the deployed position of the at least one wing grip (i.e., in the ejection operation operating mode), the wing grips protrude from the injector body. In this case, the wing grips form grip surfaces which are arranged substantially orthogonally to the longitudinal extension of the injector body. This allows the injector to be grasped, e.g., with one or more fingers of one hand on the wing grips for the purpose of an ejection operation, while the thumb of the same hand is used to hold the piston at its end and push it, if necessary. In the retracted position of the at least one wing grip (i.e., in the screwing operation operating mode), the at least one wing grip is retracted against the injector body. To this end, the injector, together with the at least one wing grip, substantially forms a uniformly longitudinal handle (without laterally protruding extensions). To this end, the at least one wing grip is integrated into the longitudinal side of the injector body. As a result, for the purpose of screwing operation, the injector body can be gripped along its length with the fingers of the first hand without any problems, while the piston is set in screwing rotation with the second hand.

The injector is particularly characterized in that the wing grip is configured in such a way that the retraction and deployment of the wing grip can be repeated. Thus, in principle, one can switch from one mode to the other at will.

The injector is characterized in that the injector body has at least one displaceable thread web, in particular one which can be pushed in and out. The at least one thread web can expediently be pushed into and out of the piston passage. On the one hand, the thread web can be pushed into the piston passage so far that the thread web acts as an internal thread with respect to the screw thread of the piston rod and a lens can be ejected by screwing movement of the piston rod. In this screwing function of the injector, the screw thread of the piston rod runs in the thread web of the injector body or the screw thread of the piston rod on the thread web of the injector body can be screwed into the piston passage or the injector body. On the other hand, the thread web can be pushed out of the piston passage or pulled away from the piston passage so that the thread web no longer acts as an internal thread with respect to the screw thread of the piston rod (and does not otherwise hinder the passage of the piston rod) and thus a lens or implant can be ejected by simple ejection movement of the piston rod (i.e., by ejection movement even without a portion of rotation).

It is particularly advantageous that the at least one wing grip and the at least one thread web are cooperatively linked so that when retracting or deploying (or pivoting in or out) the at least one wing grip, the at least one thread web is also pushed in and out. The thread web is pushed out of the piston passage when the wing grip (27, 28) is deployed and pushed into the piston passage when the wing grip is retracted.

In particular, the at least one wing grip and the at least one thread web are arranged in operative connection so that by retracting the at least one wing grip, the at least one thread web can be guided into a first position in which the at least one thread web forms a mating thread for the screw thread of the injector piston rod (i.e., for the purpose of screwing operation) and by deploying the at least one wing grip, the at least one thread web can be guided into a second position in which the at least one thread web does not form a mating thread for the screw thread of the injector piston rod (i.e., for the purpose of ejection operation).

The wing grip and the thread are connected to one another in such a way that when the wing is retracted, the wing does not deploy automatically by mechanical pressure on the thread.

In particular, the wing grip and the thread web are operatively connected to one another in such a way that when the wing grip is retracted, the wing grip cannot or cannot deploy automatically due to mechanical pressure of the piston rod on the thread web, as occurs when the piston rod is screwed in. Or to put it another way, the wing grip and the thread web are in particular operatively connected to one another in such a way that when the wing grip is retracted, the wing grip remains in the retracted position even when the piston rod exerts mechanical pressure on the thread web when the piston rod is screwed in. Deploying the wing grip can be achieved by actively manually deploying the wing grip (i.e., from outside the injector body).

If the injector contains two wings and thus a thread web in operative connection with one wing each, then the thread webs together form an internal thread for the screw thread of the piston rod when the wings are retracted. When the wings are deployed, however, the thread webs are spaced further apart than when the wings are retracted and therefore do not form an internal thread for the screw thread of the piston rod, but rather allow the piston rod to pass through the piston passage without screwing rotation of the piston rod.

The injector is advantageously characterized in that the injector body is configured in such a way that, depending on the position of the at least one wing grip and in particular on the position of the at least one thread web, the injector functions as an ejection injector or as a screw injector (dual injection function).

The at least one wing grip and the at least one thread web are expediently integrated together in at least one dual function group. The elements of the at least one dual function group are positioned along the length of the injector body.

The at least one wing grip and the at least one thread web are connected to the injector housing in an articulated manner, which in particular facilitates retracting or deploying or pivoting in or out of the wing grip and thread web.

The dual injection function is characterized in that the injector body is configured in such a way that, depending on the position of the at least one wing grip or the at least one thread web, the injector functions or can function as an ejection injector or a screw injector.

In particular, a dual injector (injector with dual function) is presented and described herein which, according to the invention, is provided with adjustable dual function groups for switching from the ejection function to the screwing function. The dual function groups can in particular be adjusted in that the at least one wing grip is configured in a retractable and deployable manner or pivotably in and out.

The injector is advantageously characterized in that the at least one retractable and deployable wing grip has an axis of rotation about which the wing grip is retractable and deployable.

The wing grip and the thread web are expediently operatively connected with one another via a pressure medium, which pressure medium is formed on the wing grip eccentrically relative to the axis of rotation of the wing grip. Such a pressure medium is also called an eccentric below.

The pressure medium or the eccentric, which is arranged eccentrically relative to the axis of rotation, holds, when the wing grip is retracted, the thread web in a first position in which the at least one thread web forms a mating thread for the screw thread of the injector piston rod so that the injector piston rod can be screwed, and holds, when the wing grip is deployed, the thread web in a second position in which the at least one thread web does not form a mating thread for the screw thread of the injector piston rod, so that the injector piston rod can be pushed.

When the wing grip is retracted, the eccentric (i.e., the pressure medium) places the thread web on the guide passage of the injector piston rod in the injector piston passage and pulls the thread web away from the guide passage of the injector piston rod when the wing grip is deployed, so that in the first case the at least one thread web forms a mating thread for the screw thread of the injector piston rod and in the second case the at least one thread web is so far away from the guide passage that the at least one thread web does not form a mating thread for the screw thread of the injector piston rod.

If the injector contains two wings and thus an eccentric (pressure medium) on each wing, the eccentrics (pressure medium) are further spaced from one another when the wings are deployed than when the wings are retracted, which simultaneously causes the thread webs to be further spaced from one another when the wings are deployed than when the wings are retracted.

The at least one thread web is expediently formed on at least one movable holder, which is movable such that the distance between the thread web and the piston passage can be changed, in particular by adjusting (i.e., deploying and retracting) the wing position. The holder is expediently attached to the injector body or is fastened to the injector body.

The distance of the thread web to the piston passage (or to the piston rod passage) or its center can be changed in that the thread web can be pushed into the piston passage or into the piston rod passage or pushed out or pulled out of the piston passage or the piston rod passage.

Due to the fact that the wing grip and the thread web are cooperatively operatively connected, the thread web is pulled out of the piston passage when the wing grip is retracted and the thread web is pushed into the piston passage when the wing grip is deployed.

The at least one movable holder can be formed as a fork with an inner leg and an outer leg. The at least one thread web is formed on the holder on the piston passage side. The at least one thread web is formed on the inner leg (i.e., on the leg that extends further into the piston passage) on the outer fork side (i.e., on the piston passage side), so that the thread web in its first position forms an internal thread for the screw thread of the injector piston rod.

Furthermore, the movable holder, in particular the fork or the legs of the fork (which form a type of (open) elongated hole) can grip or encompass the eccentric (i.e., the pressure medium), in particular in the first position of the at least one thread web and the second position of the at least one thread web and in the positions in between.

When the at least one wing is retracted and deployed about its axis of rotation, the eccentric (i.e., the pressure medium) also moves about the axis of rotation of the wing and takes the fork with it by pushing the outer leg or inner leg, wherein, when the wing is retracted, the fork on the inner leg and thus the thread web is pushed in, and when the wing is deployed, the fork on the outer leg and thus the thread web is pushed out.

The at least one wing grip is expediently attached to the injector body along its length in a retractable and deployable manner.

It is advantageous that the at least one retractable and deployable wing grip is configured as a dual wing grip, with a first wing and a second wing, so that the first wing and the second wing are fastened opposite one another (on the same injector extension) along the length of the injector body in a retractable and deployable manner.

Advantageously, the retracting and deploying movement of the two wings are synchronized, e.g., via a toothing. The toothing of the two wings can be created, e.g., by two gears or two partial gears which are fixed on and opposite the wings. The axes of rotation of the gears correspond to the axes of rotation of the respective wings.

The injector piston rod is configured on the back side (i.e., at its proximal end) with an actuating element which is used for manual operation of the piston, e.g., to manually push or turn or screw the piston.

The requirement of being able to use an injector either as an ejection or screw injector (the dual function version of an injector according to the invention) is particularly advantageously met in that the housing of the injector according to the invention is expediently formed in such a way that the housing shape can be adapted to the desired operating mode (i.e., the ejection function or the screwing function) or in that the operating mode can be set on the injector.

Each of the injectors presented herein advantageously includes an elongate injector body having a front end of the injector body and a rear end of the injector body. In the injector body or in a passage of the injector body, which leads from the front end of the injector body to the rear end of the injector body, an injector piston rod (from the rear end of the injector body towards the front end of the injector body) is expediently guided in a longitudinally (or axially) displaceable manner. The injector body contains either a loading chamber for a lens or a recess is provided for receiving a loading device with a loading chamber for a lens. The loading chamber or the recess for receiving the loading device is expediently configured in such a way that the injector piston rod can be pushed through it towards the front end of the injector body.

In particular, the recess is configured in such a way that the injector piston rod can be pushed forward through it and, if necessary, through a loading chamber inserted in the recess towards the front end of the injector body.

An injector nozzle is expediently provided at the front end of the injector body, in the direction of which the injector piston rod can be pushed forward.

It is expedient that a loading device is or can be arranged in the recess. The loading device contains in particular a loading chamber for a lens, a corneal endothelial tissue to be implanted or any other implant that is to be implanted in the eye. Optionally, the nozzle and loading chamber can be made either from one part or in two separate parts. A recess is not necessary for one-piece production.

In another embodiment of the injector, the injector is characterized in that (a) the injector body has at least one retractable and deployable wing grip, wherein the operating mode is set to ejection operation by the deployed position and the operating mode is set to screwing operation by the retracted position, and (b) the injector body has at least one thread web which, in the screwing operation, forms an internal thread for the screw thread of the piston rod and which, in the ejection operation, does not interact with the screw thread of the piston rod, e.g., in that, in ejection operation, the internal thread is offset radially further outwards with respect to the piston rod axis than in screwing operation, wherein (c) the at least one wing grip is retractable and deployable about an axis of rotation, (d) the at least one wing grip includes an eccentric (also called pressure medium), which is arranged eccentrically relative to the axis of rotation, (e) the thread web is formed on a movable holder, and/or (f) the eccentric engages in the holder so that when the wing grip is retracted or deployed, the thread web is pushed away from the piston rod axis or towards the piston rod axis by the action of the eccentric on the holder.

The invention also relates to an injector (e.g., an injector for ejecting an intraocular lens for the purpose of injecting it into an eye or an injector for implanting a corneal endothelial tissue) comprising an elongate injector body in which an injector piston rod is guided in a longitudinally (or axially) displaceable manner, wherein the injector is characterized in or additionally characterized in that the injector piston rod comprises a first stop element. Such a stop element is advantageously implemented on an injector with dual function as described above.

The stop element is advantageously characterized in that it is a displaceable stop element. In particular, the stop element is arranged in an axially (or longitudinally, i.e., along the piston rod) displaceable manner on the piston rod. The stop element expediently comprises the piston rod. The stop element is configured, e.g., as an abutting ring.

The stop element can be configured as a compressible or deformable stop element (i.e., soft stop). The stop element is made, e.g., of an elastic or deformable or compressible material, in particular silicone or TPE (thermoplastic elastomer). The compressible stop element is arranged on the injector piston rod in a displaceable manner.

The stop element is arranged on the piston rod in an axially (or longitudinally), i.e., along the piston rod, displaceable manner and configured in a deformable or compressible manner (in particular compressible at least in axial direction relative to the piston rod).

The backside of the injector piston rod is expediently provided with an actuating element which can also be called a stop support. The actuating element is used in particular to manually move the piston forward in the injector body by manually pushing or manually rotating the piston. If necessary, the actuating element acts as a restraint for the stop element (i.e., as a stop support). In addition to the first stop, which is displaceable and/or compressible, the actuating element can be used as a second stop. The actuating element, i.e., the second stop, is fixed with respect to the piston rod, i.e., not displaceable, and under normal conditions of use not compressible in the injector according to the invention, at least in the longitudinal piston orientation, (the actuating element thus acts as a so-called hard stop).

The actuating element or the stop support is an integral part of the injector piston rod or formed or fastened to the injector piston rod. The actuating element is positioned on the proximal end of the injector piston rod. The actuating element is expediently positioned in a stationary manner with respect to the injector piston rod.

Optionally, the actuating element or the stop support can include a ramp. This ramp is formed as a conical or wedge-like enlargement or thickening of the shaft in the transition from the piston rod shaft to the actuating element or to the stop support.

In the aforementioned embodiment with a first stop element, the injector body can also have at least one retractable and deployable (or pivotable in and out) and/or pushable in and out wing grip. This has the advantage that as soon as or when the injector is used to push in the lens or the corneal endothelial transplant (i.e., as an ejection injector), the wing grip or wing grips can be brought into the functional position and, at other times or for other purposes, the wing grip or wing grips can be stowed to save space.

The injector piston rod has a screw thread and the injector body has at least one displaceable thread web (or one that can be pushed in and out). Such an injector can be used as a screw injector, with the thread web or webs being able to be brought into the functional position, if necessary, by inserting the thread web or thread webs laterally into the piston passage as soon as or when the injector is to be used to insert the lens (i.e., as screw injector) and, at other times or for other purposes of the injector, the thread web or the thread webs can be removed from the piston passage.

It is advantageous that, for the purpose of the dual injection function, the at least one wing grip and the at least one thread web are cooperatively connected to one another, so that when the at least one wing grip is retracted, the at least one thread web is expediently guided from the ejection mode to the screw mode (i.e., an active position in which the thread web cooperates with the screw thread of the injector piston rod) or so that when the at least one wing grip is deployed, the at least one thread web is expediently guided from screw mode to ejection mode (i.e., an inactive position in which the thread web does not cooperate with the screw thread of the injector piston rod).

Additional advantages of the present invention result from the description below.

BRIEF DESCRIPTION OF THE FIGURES

Further advantages and features of the invention result from the following detailed description of exemplary embodiments of the invention with reference to schematic representations. In a schematic representation that is not true to scale.

DETAILED DESCRIPTION OF THE FIGURES

Figure 1:
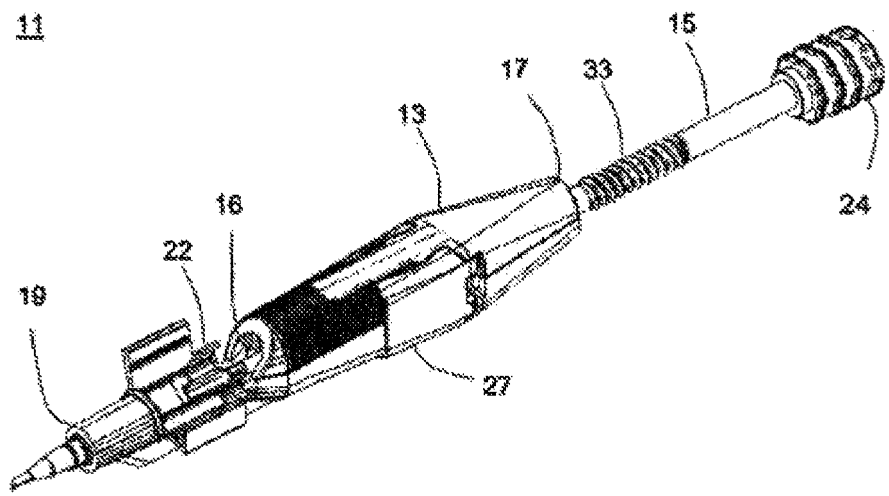
FIG. 1: shows a dual injector according to the invention with retracted wings in a perspective view.
Figure 2:
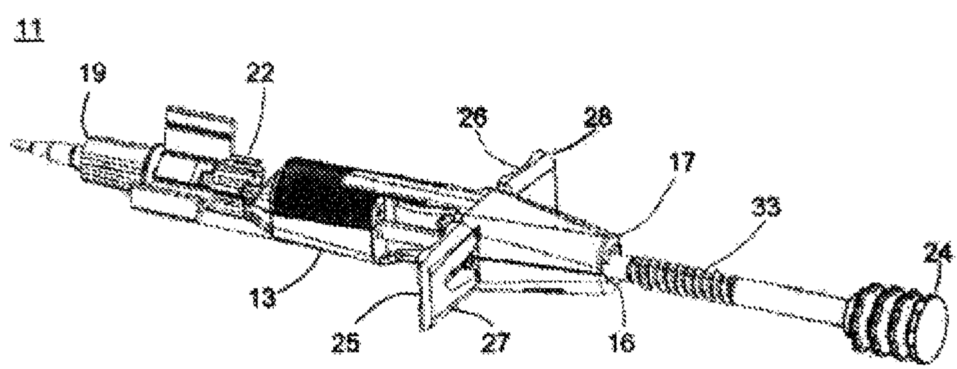
FIG. 2: shows a dual injector according to the invention with deployed wings in a perspective view.
Figure 3:
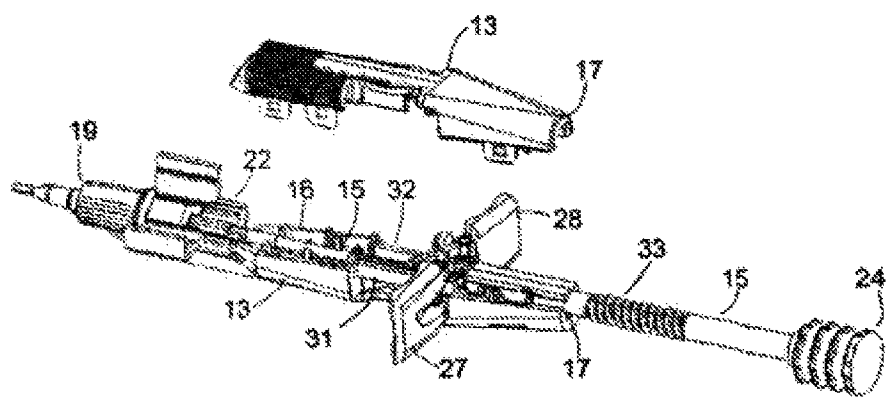
FIG. 3: shows a dual injector according to the invention with an open housing.
Figure 4:
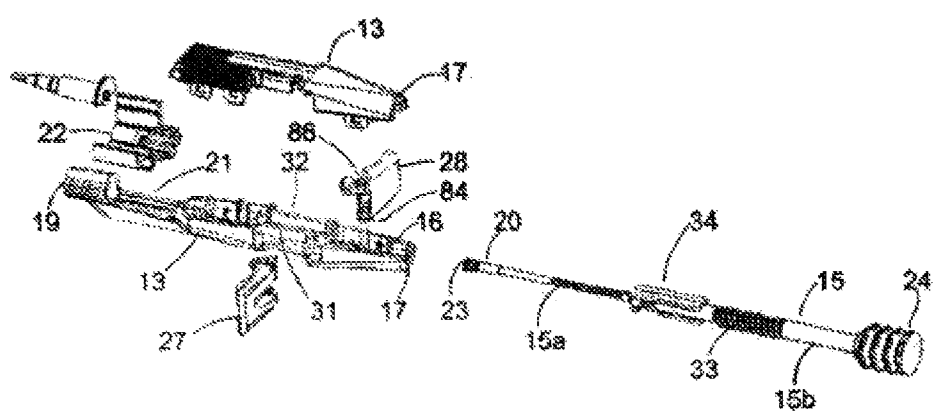
FIG. 4: shows a dual injector according to the invention, partially taken apart.
Figure 5:
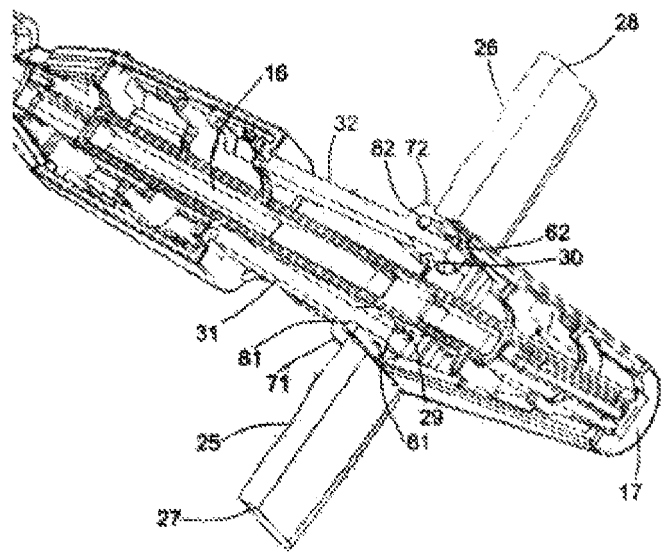
FIG. 5: shows a sectional view of the rear end of the injector with deployed wings.
Figure 6:
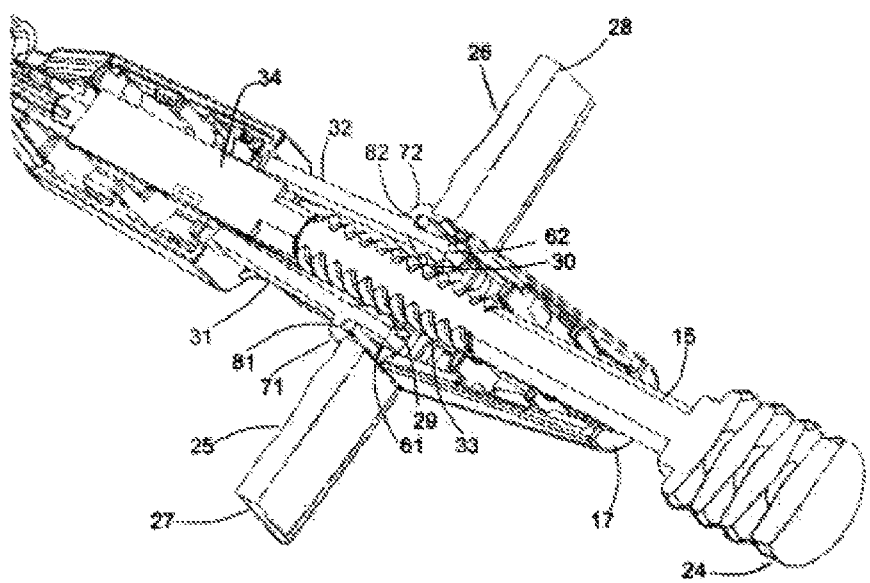
FIG. 6: shows a sectional view of the rear end of the injector with deployed wings with the piston rod inserted.
Figure 7:
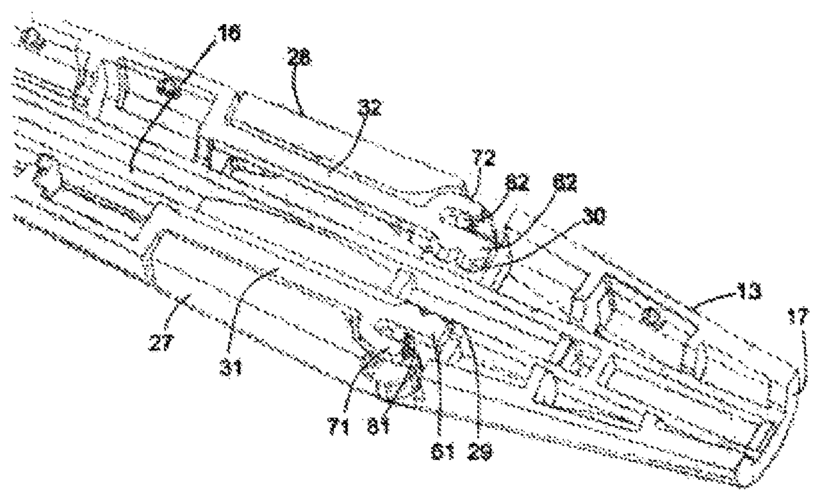
FIG. 7: shows a sectional view of the rear end of the injector with retracted wings.
Figure 8:
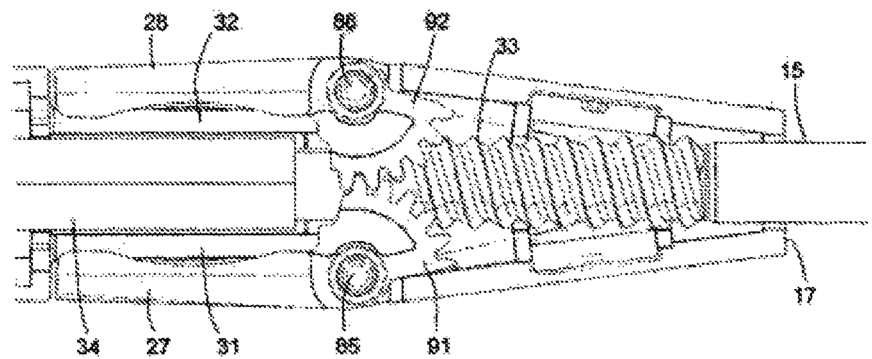
FIG. 8: shows a sectional view of the rear end of the injector with retracted wings with the piston rod inserted.

FIGS. 1 to 4 show a dual injector 11 according to the invention for an intraocular lens. In FIGS. 3 and 4, the dual injector is shown broken down into its individual parts to respectively different degrees. In the FIGS. 5 to 12, details of the dual injector are shown. The injector is used to inject the lens or a corneal endothelial graft into an eye. The dual injector combines an ejection function and a screwing function, so that the injector can be used in an ejection function as an ejection injector (FIG. 2) or in a screwing function as a screw injector (FIG. 1), wherein one function can be switched to the other and back again at any time. The injector 11 includes at least one injector housing 13 and a piston rod 15. The injector housing 13 is elongated with a first opening at a proximal end 17 through which the piston rod 15 is introduced, and a second opening at a distal end 19 through which the lens is ejected by means of the piston rod 15. The distal end 19 can be formed out as a nozzle or a nozzle can be attached thereto. The connecting passage from the first opening to the second opening is referred to below as the piston passage 16 (FIG. 1 or 3). A recess 21 in the injector housing 13 is expediently provided for receiving a loading device 22 with a loading chamber for a lens or a corneal transplant. When the loading device 22 is inserted into the recess 21, the loading chamber is positioned in the piston passage 16, so that when the piston rod 15 is passing through, a lens loaded in the loading chamber is ejected from the loading chamber towards the nozzle by means of the piston rod 15. The piston rod 15 has a distal (front) end 23 and a proximal (rear) end 24. The distal end 23 of the piston rod 15 is expediently provided with a plunger 20 (also referred to as tappet), such as an elastic or viscoelastic plunger, e.g., a plunger made of silicone. The plunger is used to gently eject the lens. The proximal end 24 of the piston rod 15 forms an actuating element which is larger than the diameter of the proximal opening 17 of the injector housing 13. The actuating element 24 can be used for manually ejecting and/or rotating (or screwing) the piston rod 15.

The piston rod 15 can advantageously be made in two parts, i.e., include a front shaft area 15*a* and a rear shaft area 15*b*, such as shown in FIG. 4, for example. These two shaft areas 15*a* and 15*b* are mounted rotatably against one another. One of the two shaft areas carries, e.g., a ball head and the other shaft area carries, e.g., a ball socket in which the ball head is rotatably mounted. FIG. 4, for example, shows a piston rod 15 which, on the one hand, has a front shaft area 15*a* with a ball socket at its rear end and, on the other hand, a rear shaft area 15*b* with a ball head at its front end. The ball head and ball socket are locked into one another so that the front shaft area 15*a* can be pushed forward in the longitudinal direction of the piston rod and pulled backwards by means of the rear shaft area 15*b*, while at the same time the two shaft areas 15*a* and 15*b* can be rotated perpendicular to the piston rod longitudinal direction.

A thread (screw thread) 33 (in particular as an external thread) is formed in the rear shaft area 15*b* of the piston rod 15. In connection with the thread 33, the actuating element 24 is used as a rotary grip for screwing the piston rod 15 into the housing 13 or for screwing the piston rod 15 back and forth (i.e., in particular for moving the front shaft area 15*a* back and forth by means of screwing the rear shaft area 15*b* back and forth). Dual function groups are formed on the longitudinal side of the injector housing 13. A dual function group includes at least one wing 27, 28 with a grip area 25, 26 for operating the injector in the ejection function position and at least one threaded area or thread web 29, 30, which acts as an internal thread web for the thread 33 of the piston rod 15 in the screwing function position of the dual function group. The dual function groups are operated by retracting and deploying or, in particular, pivoting in and out the wings 27, 28. On the one hand, the wings 27, 28 and consequently the grip areas 25, 26 can be deployed from the injector wall to the outside, where the grip areas 25, 26 act as wing grips. When deployed, the wing grips 27, 28 are formed on the injector housing 13 on the longitudinal side, protruding outwardly and, together with the actuating element 24 at the proximal end of the piston rod 15, are used as grips for manual (one-handed, if necessary) operation of the injector 11 in ejection function, in particular for pushing forward the piston rod 15 in the direction of the distal end 19 of the injector housing 13. The dual function groups are configured in such a way that when the wings 27, 28 are deployed (ejection function position), the thread webs 29, 30 are mutually spaced from one another in such a way that together they cannot grip the thread 33 of the piston rod 15 in the passage 16 or do not obstruct a passing through of the piston rod 15 through the piston passage 16. In the ejection function position of the dual function group, the thread webs 29, 30 are therefore inactive. On the other hand, the wings 27, 28 can be retracted. When the wings are retracted, the thread webs 29, 30 (away from the injector wall) are pushed inwards into the piston passage 16, where the thread webs 29, 30, placed at a certain closer distance from one another, together form an internal thread section which acts as a mating thread for the screw section 33 on piston 15.

Wing grip 27, 28 and thread web 29, 30 thus form a dual function group, which is used to switch from the ejection function to the screwing function, with wing grip 27, 28 and thread web 29, 30 interacting in such a way that when retracting or deploying wing grip 27, 28, the thread web 29, 30 is inserted in the piston rod passage 16 (or, in other words, moves towards the piston rod axis) in such a way that the thread web 29, 30 forms an internal thread for the screw thread of the piston rod 15 and thus the piston rod 15 can only be advanced by rotating in the direction of the injector nozzle, or moves away from the piston rod passage 16 (or, in other words, moves away from the piston rod axis in such a way) that the thread web 29, 30 no longer forms an internal thread and thus the piston rod 15 can be advanced by pushing.

The piston rod 15 is expediently guided in the injector housing 13 (with as little play as possible), regardless of the type of function—ejection function or screwing function. A guide can be achieved, for example, in that, on the one hand, a guide structure 34 is formed on the piston rod 15 and, on the other hand, counter structures (e.g., a kind of guardrail for the guide structure 34) adapted to the cross-section of the guide structure 34 are configured as inner wall areas of the piston rod passage 16 at the injector housing 13. For example, the guide structure 34 can expediently include the ball socket. In FIG. 4, the guide structure 34 is formed, for example, at the rear end of the front shaft area 15*a* as a thickened piston rod cross-sectional area with a ball socket recess. The recess is formed in such a way that it can receive the ball head which is formed at the front end of the rear shaft area 15*b*. The guide structure 34 thus advantageously is used as a guide for the piston rod 15, in particular the front part 15*a* of the piston rod 15, and on the other hand as a ball socket for receiving the ball head of the rotatable rear part 15*b* of the piston rod 15. The front shaft area 15*a* is not rotatable in the embodiment shown here (in particular due to its non-circular cross-section and a corresponding piston passage cross-sectional configuration), so that it is ensured that a lens is not rotated when the piston rod 15 is pushed forward.

Wing grip 27, 28 and the associated threaded area 29, 30 are each part of a function group, i.e., the dual function group. They are shown in particular in FIGS. 5 to 9. Expediently, two dual function groups are provided on the longitudinal side of the injector housing 13. An advantageous dual function group includes a wing 27, 28 which is pivotable or retractable/deployable about a pivot axis 35, 36 with respect to the injector housing 13, with an eccentric 81, 82, and a fork holder 31, 32 which is deflectable with respect to the injector housing and includes two legs, one inner leg 61, 62 and one outer leg 71, 72. A threaded area 29, 30 is formed on the fork holder 31, 32. As shown in the figures, the threaded area 29, 30 can be formed on the outside of the leg on the inner leg of the fork (FIGS. 5 to 8). Fork holder 31, 32 and wings 27, 28 are formed separately from one another in a deflectable or pivotable manner on the injector housing 13 and arranged to one another in such a way that the wing 27, 28 engages between the legs of the fork holder 31, 32 by means of eccentrics 81, 82, so that when the wing 27, 28 is deployed, the fork is pulled away from the piston passage 16 by means of eccentrics 81, 82 and thus the thread web 29, 30, which is formed on the fork holder 31, 32 or in particular on the fork leg, is pulled out of the piston passage 16, and when the wing 27, 28 is retracted, the fork is pushed towards the piston passage 16 by means of the eccentric 81, 82 and consequently, the thread web 29, 30 is pushed into the piston passage 16.

The applicant found out from preliminary tests that quite high forces act on threaded parts which are used as internal threads on the screw thread of the piston rod when screwing. These forces drive the threaded parts away from the piston rod when screwing, so that in return quite a high force has to be applied to hold the threaded parts in position and thereby maintain the screwing mode. The embodiment according to the invention shown in FIGS. 1-9 with an eccentric on the retractable/deployable wing for pushing in a displaceable threaded part proved to be particularly advantageous since the retracted wings are not deployed automatically by the pressure exerted on the thread when screwing. This means that the surgeon does not have to be careful to press the wings during the screwing process, but can focus on the forward movement of the piston and thus the lens to be injected. In the present embodiment, this is achieved in that the forces acting on the thread are transmitted to the wing rotation axis 35, 36 in such a way that the resulting forces substantially do not produce any opening effect on the wings.

Figure 9:
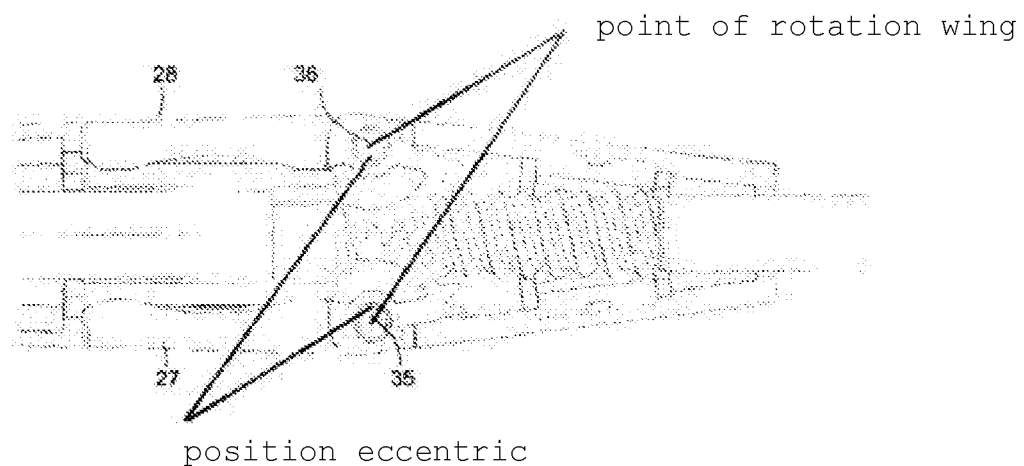
FIG. 9: shows a sectional view of the rear end of the injector with retracted wings with the piston rod inserted, the center of rotation of the wings and the position of the eccentrics being marked.

In the embodiment shown in FIG. 9, the grip extension of the wing 27 or 28 from the axis of rotation 35 or 36 and the eccentric 61 or 62 spaced apart from the respective axis of rotation 35, 36 form an angle, e.g., of approximately 90 degrees around the respective axis of rotation 35, 36. In particular, angle ranges of 90°±5° 90°±2° or 90°±1° are useful. The forces acting on the thread webs 29, 30 by means of screw thread 33 can be transmitted to the eccentrics 61, 62 in the retracted wing position in such a way that the resulting forces substantially do not create an opening effect on the wings but rather maintain the retracted position. In particular, the constructive embodiment is designed in such a way that the resulting force of the screwed piston 15 acts on the respective eccentric 61, 62 in a direction which is directed from the eccentric to the axis of rotation of the wing, or which is directed from the eccentric in relation to the injection direction on or in front of the axis of rotation (or in front of the point of rotation in FIG. 9) of the respective wing.

The fork holder 31, 32 is shaped as a holder fastened to the injector housing 13 with a first end and with a two-legged bifurcation formed on the free, second end. Due to the constructive structure and the nature of the material, the bifurcated end of the holder 31, 32 is movable or pivotable with respect to the end fixed on the injector housing or integrated in the injector housing. Alternative embodiments are conceivable, for example the first end of the fork holder could be attached to the housing by means of an axis of rotation. The fork holder 31, 32 expediently extends along the longitudinal direction of the injector housing and replaces a portion of the injector housing wall, which creates space for the displacement of the thread webs 29, 30.

For the rotatable anchoring of the wings in the housing 13, each wing 27, 28 includes two axis elements 83, 84, 85, 86 which, e.g., can be formed as pins or indentations. Corresponding counter structures to the axis elements 83, 84, 85, 86 are formed in the housing for receiving the wings. The axis elements or a connecting line between the two axis elements 83, 84 or 85, 86 of a wing 27, 28 defines the axis of rotation or pivot axis 35, 36 of the wing 27, 28. Furthermore, each wing 27, 28 includes a grip area 25 for operating the injector in the ejection function position. Each wing 27, 28 has an eccentric 81, 82, by means of which a displaceable threaded area 29, 30 can be brought into an ejection function position or into a screwing function position. In the screwing function position (FIGS. 1, 7 and 8), the threaded area 29, 30 acts as an internal thread web for the screw thread 33 of the piston rod 15. In the ejection function position (FIGS. 2, 5 and 6), the threaded area 29, 30 ideally is pushed out of the piston passage 16 towards the housing wall or towards the axis of rotation of the respective dual element 27, 28, so that the threaded area 29, 30 cannot hinder the piston rod 15 with screw thread 33 from passing through the piston passage 16. The position of the respective eccentric 81, 82 is eccentric with respect to the respective wing axis of rotation 35, 36. The wing axis of rotation 35, 36 is defined by two axially spaced axis elements 83, 84, 85, 86 and is configured in such a way that, where the structural formation of the axis of rotation 35, 36 is interrupted (i.e., between the axis elements 83, 84, 85, 86), the eccentric 81, 82 is formed eccentrically with respect to the wing axis of rotation 35, 36. The eccentric is configured as a cylindrical shape on the wing 27, 28, e.g., as a circular cylinder, and expediently aligned parallel to the axis of rotation 35, 36 of the respective wing.

By changing the wings 27, 28 from a first position (deployed wings) to a second position (retracted wings), a function change from the ejection function to the screwing function can be made. When the wings 27, 28 are changed from a first position (deployed wings) to a second position (retracted wings), the eccentrics 81, 82 also move at the same time from a first position (with a first mutual distance when the wings are deployed) to a second position (with a second, shorter mutual distance when the wings are retracted).

In the ejection function position, the wing element 27 protrudes outward from the injector housing (in particular pivoted away from the injector housing and blocked against further pivoting towards the actuating element 24 or towards the proximal housing part), while the threaded area 29, 30 at the same time is in a rest position or pulled out of the piston passage 16 and in functionless position (i.e., out of function). In the screwing function position, the threaded area 29, 30 is pressed inward into the piston passage 16, at the same time the wing 27, 28 is retracted and forms part of the injector housing wall or is lowered into the injector housing wall. The changeover from one functional position to the other can be carried out expediently by turning or retracting/deploying about the axis of rotation 35, 36.

The movement of the two wings 27, 28 and thus of the two dual function groups can be synchronized by a toothing (91, 92) so that only one wing 27 or 28 is retracted or deployed and the second acts symmetrically thereto. For this purpose, each of the two wings 27, 28 has a gear or at least a partial gear 91, 92 which is concentric with respect to its axis of rotation 35, 36. The two gears or partial gears are in particular configured and installed on the housing 13 interlocked in such a way that the two wings can only be deployed and retracted synchronously.

In the ejection function, the deployed wings 27, 28 together with the actuating element 24 of the piston rod are used as grips for manual operation of the injector for pushing the piston rod 15 (substantially straight) forward in the direction of the distal end 19 of the injector housing 13. When the wings 27, 28 with the eccentrics 81, 82 are deployed, the thread webs 29, 30 are spaced apart from one another in a first position in such a way that the piston rod 15 can be pushed through the piston passage 16 without hindrance from the thread webs 29, 30. The dual injector is operated in the ejection function position, for example, by simultaneously pressing on the actuating element 24 from behind on the one hand, and, on the other hand, on the wing grip areas 27, 28 in the opposite direction of force on the other hand—this is done with one hand (especially e.g., by one-handed three-finger grip).

In the screwing function, the thread webs 29, 30 which are positioned inwards, i.e., into the piston passage, due to a second eccentric position, are used as internal threads for the piston rod thread 33, so that the piston rod 15 can be screwed in by a manual rotating actuation of the actuating element 24 and thereby causing a pushing of the piston rod 15 forward in the direction of the distal end 19 of the injector housing 13 while rotating about its own axis (screwing movement). The dual injector is operated in the screwing function position, for example, by simultaneously rotating the actuating element 24 with one hand, on the one side, and holding the injector housing 13 with the other hand (i.e., e.g., by two-handed operation), on the other side.

Figure 10:
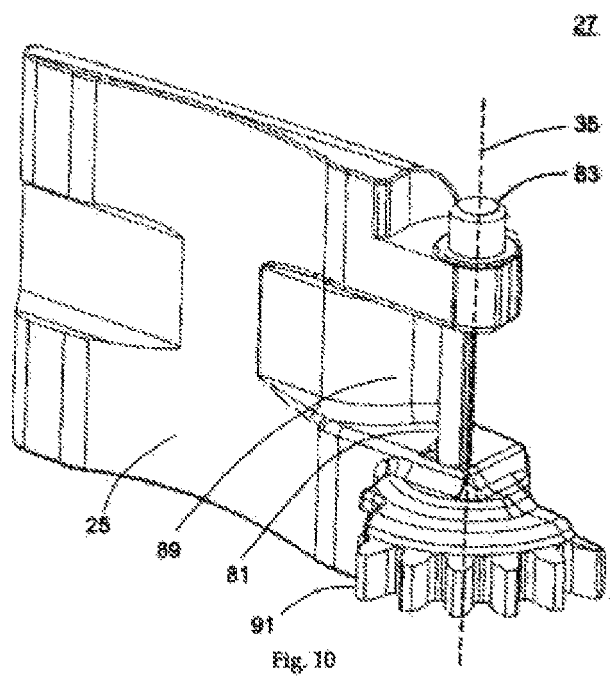
FIG. 10: shows a left wing in perspective view.
Figure 11:
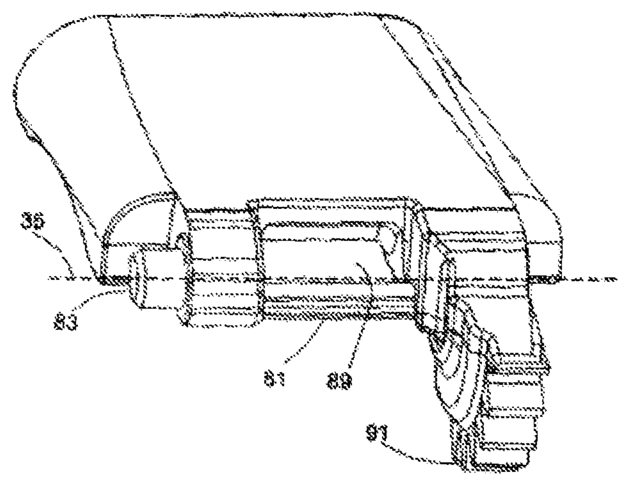
FIG. 11: shows a left wing in a further perspective view.
Figure 12:
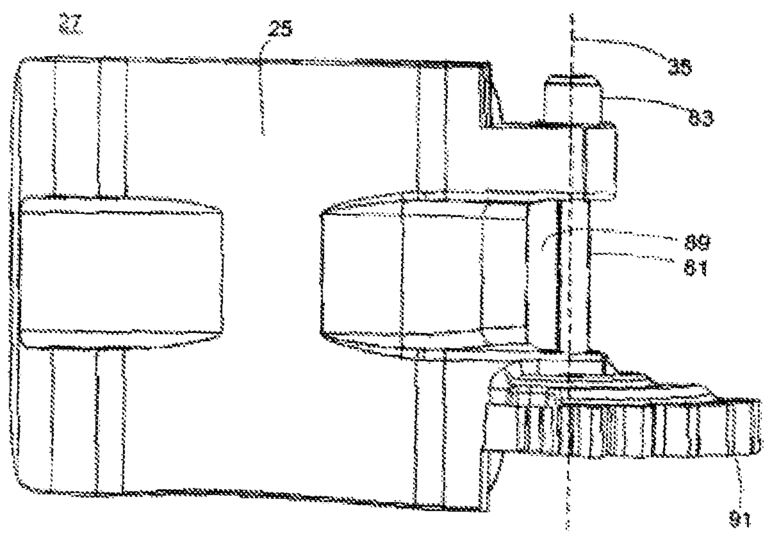
FIG. 12: shows a left wing in a further perspective view.

FIGS. 10, 11 and 12 show an exemplary wing 27, as it can be used, for example, in the embodiment according to FIGS.

1 to 8. FIGS. 10 and 11 show in particular the offset between the eccentric 81 and the axis of rotation 35 (axis of rotation indicated as a dashed line), which is defined by the axis extension of the axis element 83. This offset corresponds to the offset shown in FIG. 9 between the point of rotation 35, 36 of the respective wing 27, 28 and the corresponding eccentric position. Because the eccentric 81 is formed parallel to the axis of rotation 35 of the wing 27, but between the spaced-apart elements 83, 85 which define the axis of rotation 35 of the wing 27, the eccentric can be enclosed by the fork legs 61, 71 in such a way that when retracting/deploying the wing 27, the fork legs 61, 71 are displaced in an interacting manner with the eccentric 81 by the eccentric movement. So that the holder 31, 32 or its bifurcated legs 61, 62, 71, 72 can encompass the eccentric 83, 85, a recess 89 is provided on the wing 27, 28. While in FIGS. 2 to 4, in contrast to wing 28, the wing 27 was illustrated with an optionally enlarged recess, in FIGS. 10 to 12 such an enlargement of the recess is dispensed with.

So that the injector 11 is as inexpensive as possible, it is made substantially from a suitable plastic, e.g., by injection molding. In particular, the housing 13 including fork holder 31, 32, or several housing parts, the piston rod 15, the wings 27, 28, and the loading chamber 22 are produced from a plastic, e.g., ABS, polycarbonate and/or polypropylene.

FIGS. 13 to 17 show a schematic embodiment of a dual injector 111 in combination with a stop element 141. Here, the ejection and screwing position of the wings are shown in the same figure opposite each other. The left wing 128 abuts with its grip area 126 on the injector housing 113 along its length and is thus shown in the screwing function position. The right wing 127 protrudes substantially at a right angle from the injector housing 113 and is thus shown in the ejection function position. This type of illustration is only used to make it clear that both functions can be used or that you can choose or switch between them. For details on the functionality in the ejection and screwing position, reference is also made to FIGS. 1-13.

To use the dual injector 111 as an ejection injector, both wing grips 127, 128 should be deployed. By pressure on the actuating element 124 (e.g., by thumb or palm of the hand) and by simultaneous counter pressure on the gripping surfaces 125 of the two wings 127, 128, the piston rod 115 or its tip 123 can be pushed towards the distal end 119 of the injector housing 113 (and thus to an injector nozzle integrated or mounted there).

To use the dual injector 111 as a screw injector, both wing grips 127, 128 should be retracted. In this screwing function position of the dual elements 127, 128, the piston rod 115 can be driven into the piston passage 116 by rotating the actuating element 124 about the longitudinal axis of the piston rod 115.

The wing grip 127 has a gripping surface 125 which is advantageously provided with ridges to prevent slipping or for a good grip. In the ejection function position of the wing 127, the grip surface 125 is aligned substantially perpendicular to the piston rod ejection direction and the grip surface 125 points towards the distal piston rod tip. In the screwing function position, however, the wing 128 is nestled against the injector housing 113 and forms, together with the outside of the housing 113, substantially a continuous grip handle.

The stop element 141 (as indicated in FIGS. 13 to 17), which comprises the piston rod 115 or is mounted on it, is made of a deformable and/or compressible material, e.g., made of silicone material or TPE (thermoplastic elastomer), from a 1 mm to 6 mm, 2 mm to 5 mm, or 3 mm to 4 mm thick disc of one of these materials. The Shore hardness of the silicone material is at least 20 Shore and at most 80 Shore, 30 Shore to 70 Shore, or 40 Shore to 60 Shore. The stop element 141 is ring-like, i.e., configured as a ring (ring disk), in particular as a closed ring (closed ring disk).

Below, the advantageous use of a stop element 141 in combination with an ejection injector, a screw injector or a dual injector 111 will be addressed.

Figure 13:
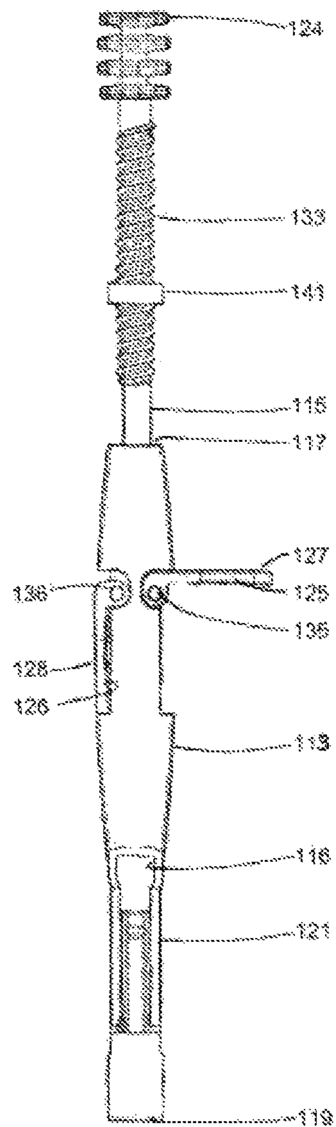
FIG. 13: shows a dual injector with its piston rod in a first feed position (first feed position, starting position)

In FIG. 13, the stop element 141 is displaceably mounted on the rear area of the shaft of the piston rod (in comparison with FIGS. 1-4). In a starting position (FIG. 13), the stop element 141 can be, e.g., displaceably mounted approximately centrally on the rear area of the shaft of the piston rod 115. In particular, the stop element 141 can be positioned in front of the actuating element 124 at a certain distance, where it marks a certain feed position in a notch (not shown) and/or sitting on the thread 133, at which feed position the piston rod 115 is stopped before the further advancement, e.g., as soon as the stop element hits the injector body. This is particularly useful in the case of preloaded injector systems (i.e., systems where the lens is already loaded into the injector upon delivery). Here, the stop element 141 is used, on the one hand, to set and maintain a certain feed position of the distal end 123 of the piston rod 115, at which feed position a stop can be made and certain preparatory steps can be carried out with the loading chamber still open. These preparatory steps can include, for example, placing the haptics of the lens on the optics by means of the silicone plunger on the piston rod or removing the lens holder with the piston rod pushed forward.

In FIG. 13, the piston rod 115 is inserted into the injector housing 113 in a first feed position. This feed position can be secured by a spring clip (the concept of spring clip securing is not shown in FIGS. 13-17, but is indicated in FIG. 18 with reference numeral 251, which shows a spring clip lock), so that this first position can be more easily found, set and held, if necessary. A further pushing after overcoming the spring force is provided. The spring clip prevents the piston from falling out of the back of the injector housing, since the piston rod can be moved forward, but no longer backward from the first feed position. The stop element 141 is displaceably attached to the rear shaft part of the piston rod 115, which protrudes clearly visible from the housing 13. A displaceable stop element 141 is hereinafter also referred to as a carriage. The displaceable stop element 141 is formed to be larger on its outer diameter than the opening at the proximal end 117 of the injector housing 113. This ensures that the stop element 141 can be pushed backwards on the piston rod 115 towards the actuating element 124 when the piston rod 115 is pushed into the injector housing 113 after hitting the proximal end 117 of the injector housing 113.

Figure 14:
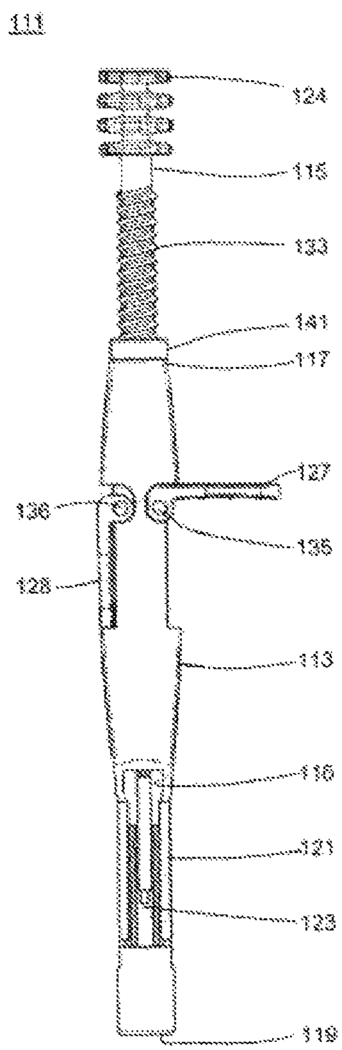
FIG. 14: shows a dual injector with its piston rod in a second feed position (second feed position)

FIG. 14 shows the second feed position of the piston rod 115. Here the stop element 141 abuts the injector housing 113 for the first time. However, the stop element 141 still has the same position with respect to the piston rod 115 as in FIG. 13. In or from this piston position, preparatory steps can be carried out with the loading chamber still open. These preparatory steps can include, for example, placing the haptics of the lens to the optics by means of the silicone plunger on the piston rod, or removing the lens holder with the piston rod pushed forward. Further preparatory steps are conceivable, but always include pushing the piston rod forward until the stop element noticeably strikes the injector housing. Only then the loading chamber is closed and the piston rod advanced further.

The stop element 141 is optionally located in a piston groove or in the thread (not visible because it is located on the piston rod under the attached stop element). It therefore may require a certain overcoming force (e.g., 3-4 Newton) to push the piston rod 115 from the second feed position further into the injector housing 113. This overcoming force is expediently felt by the user as a stop or increased resistance so that, on the one hand, the insertion can be stopped perceptibly and visibly precisely at this second feed position (and passing over the second feed position is thus prevented) and, on the other hand, by overcoming the resistance the piston rod 115 can be pushed further into the injector housing controllably and with little force. After the second feed position has been overcome, the stop element 141 slides backwards when the piston rod 115 is pushed or turned into the piston passage 116 on the piston rod 115 up to or against the stop on the actuating element 124.

Figure 15:
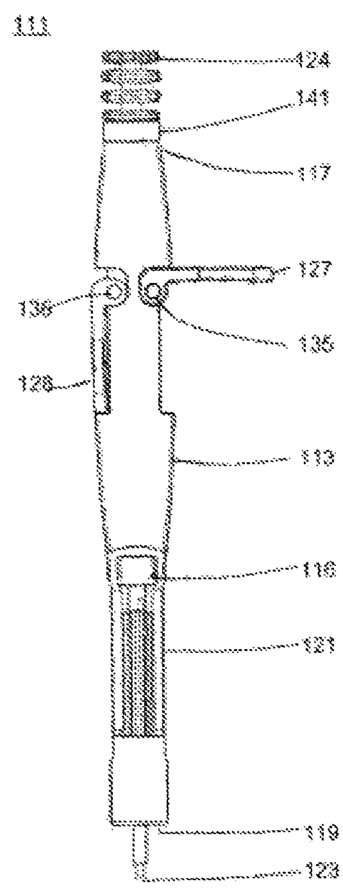
FIG. 15: shows a dual injector with its piston rod in a third feed position (third feed position)

In FIG. 15, the piston rod 115 is inserted into the injection housing 113 to a third feed position. In this position, the stop element 141, on the one hand, still abuts on the proximal end 117 of the injector housing 113 and, on the other hand, the stop element 141 abuts at the same time on the actuating element 124. In this third position, the lens should ideally be fully ejected.

Figure 16:
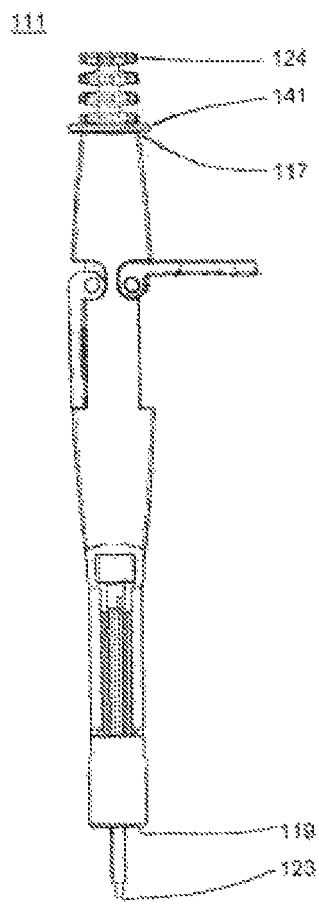
FIG. 16: shows a dual injector with its piston rod in a fourth feed position (reserve position)

In the event that the lens is not yet fully ejected for any reason (e.g., deliberately choosing a short piston rod to avoid the exit of the silicone plunger, increased friction due to the use of highly viscous viscoelastic liquid, low temperatures, slow and stagnant injection, etc.), the stop element 141 can expediently be contracted or compressed (insofar as it is made of a deformable or compressible material, e.g., made of silicone) by a maximum of a few millimeters with increasing manual force until the lens is fully ejected. The stop element 141, which is compressed or contracted due to manual pressure, is shown in FIG. 16. In this case, the piston rod 115 is pushed in up to a fourth feed position. By compressing the stop element 141, the piston rod tip 123 can be used to reach a reserve feed area in order to be able, if necessary, to fully eject a lens from the injector which has not yet been fully ejected in the third feed position. Due to the additional force required to contract the stop element, the surgeon is prepared for the imminent ejection of the lens in a tactile manner and any unintentional pushing of the piston tip or a plunger sitting on it too far is prevented.

Figure 17:
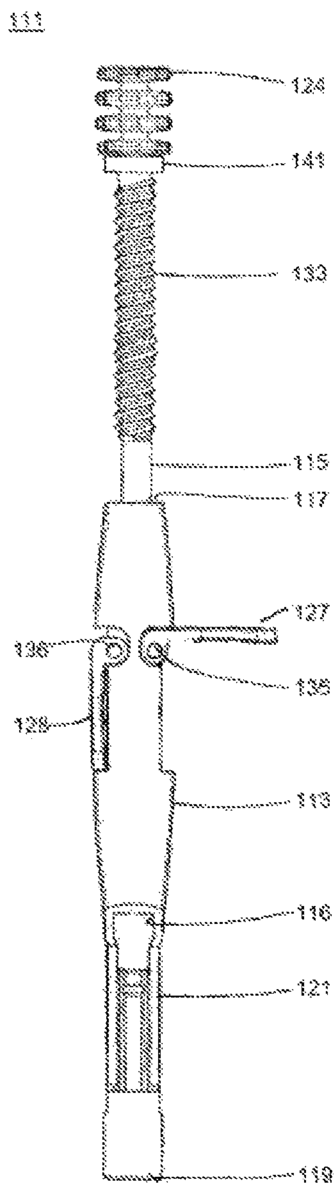
FIG. 17: shows a dual injector with its piston rod in a first feed position (alternative starting position)
Figure 18:
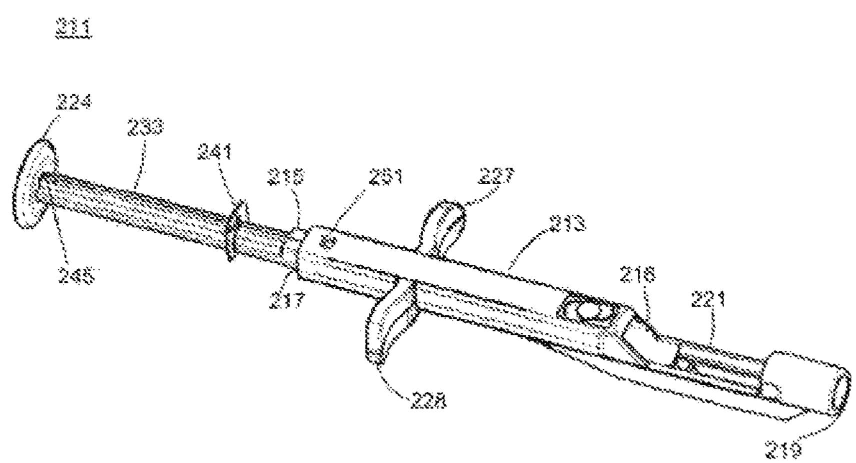
FIG. 18: shows an ejection injector with ramp and carriage with its piston rod in a first feed position (first feed position).

In an alternative starting position, as shown in FIG. 17, the stop element 141 can be arranged adjacent to the actuating element 124 from the start. In this case, the stop element 141 is primarily used to set and control the exact end position of the distal end 123 of the piston rod 115, so that the user first feels a clear impact of the piston rod or the actuating element 124 on the housing 117 shortly before ejecting the lens and a plunger sitting on the piston rod tip 123 is not pushed unnecessarily far out of the injection nozzle. If necessary (that is to say when the lens has not yet exited completely), however, a further advancement of the piston 115, expediently a few millimeters, is possible with additional force, in that the stop element 141 is contracted. In this way, a flexible reserve area is created for the feed length of the piston rod 115 or its tip 123 (without the clear, first noticeable stop being lost). This alternative starting position (according to FIG. 17) is advantageously used in systems in which no further preliminary steps are necessary during the injection process.

In an alternative embodiment according to FIG. 18, an ejection injector 211 with a displaceable and substantially incompressible stop element 241 (also called a carriage) is presented. In this context, incompressible means that the stop element 241 is substantially incompressible, at least when it is subjected to normal use of the ejection injector 211. The ejection injector has wing grips 227, 228 on the injector housing 213 and an actuating element 224 at the proximal end of the piston rod 215. The piston rod 215 has a ramp 245 in the rear area of the piston rod shaft 233, which ramp is configured to rise from the piston rod shaft to the piston rod end or to the actuating element 224. The stop element 241 is seated in a piston groove (not visible) of the piston rod 215.

From the feed position shown in FIG. 18 (similar to the first feed position shown with reference to FIG. 13), the piston rod 215 can be pushed into the injector housing 213 in two stages and optionally in a reserve stage.

From the first feed position shown in FIG. 18, the piston rod 215 is pushed further into the injector housing 213 until the carriage 241 abuts on the proximal end 217 of the injector housing 213 (in particular without the carriage 241 being axially moved with respect to the shaft of the piston rod 215). This position is called the second feed position (similar to the second feed position shown with reference to FIG. 14). The carriage is still seated in the piston groove of the piston rod 215, provided a piston groove is provided on the shaft.

If the piston rod 215 is pushed further into the injector housing 213, the carriage 241 is pushed backwards along the shaft 233 of the piston rod 215 at the same time, and, if necessary, pushed onto the ramp 245. The carriage 241 can be pushed largely without resistance. As soon as the ramp 245 hits the proximal end 217 of the injector housing 213, the piston rod 215 is inserted into the injection housing 213 up to a third feed position (similar to the third feed position shown with reference to FIG. 15). In this third feed position, the lens should ideally be fully ejected.

If, however, the lens is not fully ejected in the third feed position, the ramp 245 can be pressed into the edge of the injector housing 213 at its proximal end 217 by further pressure. The end position reached by the piston rod 215 can be called the reserve position. The ramp 245 can only be pushed into the proximal end 217 of the injector housing 213 with increased manual force on the part of the surgeon.

So that the stop element 241 can slide substantially without friction over the ramp 245, the stop element 241 is configured to be flexible, which can be achieved by a suitable choice of material and/or structurally determined shaping of the ramp 245 and stop element 241. For example, the stop element (or the carriage) 241 can be made as a U-shaped clamp element from substantially (under the intended application conditions) incompressible material, which expands plastically when it is pushed out of the piston notch and thereby can be moved along the piston and can abut the ramp 245 until the stop element 241 effectively abuts the actuating element 224.

Application examples for the use of injectors with a stop element follow.

Application Example 1

A dual injector 111 as described above (e.g., FIGS. 13-16) is provided with injector housing 113 and piston rod 115. A displaceably attached stop element 141 made of a silicone material is provided on the piston rod 115. The stop element is configured, e.g., as a ring-shaped element made of a compressible material. A loading device (not shown in the figures) for receiving a lens or with an already preloaded lens is inserted in the recess. The piston rod 113 is brought into the first feed position or is already in it. The first feed position is characterized in that the piston rod is inserted to some extent into the proximal opening 117 of the injector housing 113. Starting from this first position, the piston rod 115 should be guided to the lens with its front end 123 (which has an elastic or viscoelastic plunger) when the piston rod 115 is advanced further (by ejecting or screwing) and the lens is ejected (through a nozzle) in front of the piston rod 115 when the piston rod 115 is advanced further until the lens is ejected from the distal end 119 of the injector housing 113 or from the nozzle formed or attached at the distal end 119. The first feed position can be secured by clicking into a spring clip (not shown in FIGS. 13-16). When the piston rod 115 is pushed into the piston passage 116, the displaceable stop element 141 is pushed together with the piston rod, so to speak piggyback on the piston rod 115, from the first feed position towards the proximal opening 117 of the injector housing 113 until the stop element 141 strikes the edge of the proximal opening 117 of the injector housing and the piston rod 115 can only be pushed in further if the piston rod 115 is pushed through the stop element 141 or the stop element 141 is held up on the edge of the proximal opening of the injector housing and slides backward along the piston rod. The position of the piston rod 115 when the stop element 141 first strikes the edge of the proximal opening 117 of the injector housing is called the second feed position. This position is easily recognizable visually and, depending on the strength of a clamping effect of the stop element 141 on the thread of the piston rod or if there is a transverse groove on the piston rod 115, it can also be perceived tactilely, as a further pushing forward can be felt due to a higher resistance (due to the friction of the stop element on the piston rod or at least temporarily when overcoming the transverse groove).

The second feed position enables the user to carry out further preparatory steps even before the loading chamber is closed. A typical preparatory step could, for example, be the mechanical placing of the lens haptics to the lens optics by means of the silicone plunger on the piston rod 115. In the case of preloaded hydrophilic lenses, it also makes sense to advance the piston rod 115 even before removing the lens holder (a component that locks preloaded lenses in the loading chamber during transport and storage) to a point so that the lens no longer can slip out of the loading chamber in the proximal direction after the lens holder has been removed. Both preparatory steps are carried out automatically by moving the piston rod forward while the loading chamber is still open. Further preparatory steps are conceivable, but are always carried out in that the piston rod 115 is pushed forward until the stop element 141 noticeably strikes the proximal opening 117 of the injector housing 113. The loading chamber is only closed after the preparatory step has been carried out.

In order to push the piston rod 115 from the second feed position further into the passage of the injector housing 115, the piston rod 115 is pushed through or screwed in the displaceable stop element 141, which is locked at the edge of the proximal opening 117 of the injector housing. As soon as the stop element 141 strikes the actuating element 124 (i.e., is sandwiched between the actuating element 124 and the edge of the proximal opening 117 of the injector housing), the third feed position of the piston rod 115 is reached. If the lens has not yet been fully ejected in this third feed position, then—insofar as the stop element 141 consists of a compressible material—the stop element 141 can be contracted by additional pressure on the actuating element 124, whereby the piston rod 115 moves forward a little further (e.g., up to a few millimeters) and ejects the lens.

The application of a displaceable stop element has been described here (comparatively using the example of an incompressible carriage and using the example of a compressible carriage).

Application Example 2

In contrast to the previous application example 1, the silicone ring is slipped onto the rear part of the piston rod from the start and pushed up to the actuating element (e.g., FIG. 17) (in this example the silicone ring does not necessarily have to be slidable on the piston rod). This arrangement is most useful in systems in which no further preparatory step is necessary. When the piston rod is pushed forward, the second feed position (similar to the aforementioned second feed position in application example 1) is not felt tactilely and is therefore passed over because the silicone ring is already at the back end of the actuating element. If necessary, the second feed position could be set on the basis of visual markers. As soon as the silicone ring is sandwiched between the actuating element and the proximal end of the injector housing, the third feed position of the piston rod is reached. If the lens is not yet fully ejected in this third feed position, additional pressure on the actuating element 124 can be used to compress the silicone ring 141, whereby the piston rod advances yet a few millimeters and ejects the lens.

The application of a compressible stop element (using the example of a silicone ring) was described, herein.

Comparison of Application Examples 1 and 2

In the two examples, application example 1 and application example 2, a feed reserve is implemented in that an additional feed is achieved by compressing the stop element 141 only by significantly more forceful pressure or screwing. For this purpose, the material of the stop element 141 can be compressed under manually applied force. This type of stop can also be referred to as a soft stop.

In order to achieve a useful extra piston path, the silicone ring thickness is expediently in the range from at least 1 mm to at most 6 mm, in the range from 2 mm to 5 mm, or in the range from 3 mm to 4 mm. The Shore hardness is in the range of at least 20 Shore and at most 80 Shore, in the range from 30 Shore to 70 Shore, or in the range from 40 Shore to 60 Shore.

In the first exemplary embodiment, the advantageous properties of two different stop elements are combined:

a) a displaceable stop element (carriage), and b) a compressible stop element (soft stop).

The combination of the two stop features is particularly advantageous for use with a screw injector or a dual injector, which can be used as a screw injector or a pressure injector.

Application Example 3

An ejection injector 211, as described, e.g., in FIG. 18 above, is provided with injector housing 213 and piston rod 215. The piston rod 215 has a ramp wedge 245 that rises towards the actuating element. A displaceably attached stop element (also called a carriage) 241, which is essentially incompressible, is provided on the piston rod 215.

The stop element can be configured, e.g., as a U-shaped clamp element (as shown in FIG. 18).

A loading device (not shown) for receiving a lens or with an already preloaded lens is inserted in the recess or can be inserted therein. The piston rod 213 is brought into the first feed position or is already in this position. The first feed position is characterized in that the piston rod is inserted somewhat into the proximal opening 217 of the injector housing 213. Starting from this first position, the piston rod 215 is to be guided to the lens by further advancing by pushing with its front end 223, and the lens is to be pushed in front of the piston rod 215 as the piston rod 215 is advanced further (through a nozzle (not shown in the figures)) until the lens is ejected from the distal end 219 of the injector housing 213 or the nozzle formed or attached to the distal end 219. The first feed position can be secured by means of a spring clip. When the piston rod 215 is pushed into the piston passage 216, the displaceable stop element 241 is pushed together with the piston rod, so to speak piggyback on the piston rod 215, from the first feed position towards the proximal opening 217 of the injector housing 213 until the stop element 241 strikes the edge of the proximal opening 217 of the injector housing and the piston rod 215 can only be pushed in further if the piston rod 215 is pushed through the stop element 241 or the stop element 241 is held up on the edge of the proximal opening of the injector housing and slides backward along the piston rod. The position of the piston rod 215 at the first stop of the stop element 241 at the edge of the proximal opening 217 of the injector housing is called second feed position. This position is easily recognizable visually and, depending on the strength of a clamping effect of the stop element 241 on the shaft of the piston rod or if there is a transverse groove on the piston rod 215, it can also be perceived tactilely, as a further pushing forward can be felt due to a higher resistance (due to the friction of the stop element on the piston rod or at least temporarily when overcoming the transverse groove).

In order to push the piston rod 215 from the second feed position further into the passage of the injector housing 213, the piston rod 215 is pushed through the displaceable stop element 241, which is held at the edge of the proximal opening 217 of the injector housing 213. As soon as the ramp wedge 245 strikes the injector housing 213, in particular at the edge of the proximal opening 217 of the injector housing 213, the third feed position of the piston rod 215 is reached. If the lens is not yet fully ejected in this third feed position, ramp wedge 245 and injector housing 213 can be pressed against each other by additional pressure on the actuating element 224 (e.g., at least 3 Newton, or at least 5 Newton), whereby by deformation of the injector housing edge at the proximal opening 217 and/or the ramp wedge 245, if necessary, the piston rod 215 advances a little further (e.g., up to a few millimeters) and ejects the lens.

The use of a displaceable stop element (using the example of a substantially incompressible carriage) in combination with a ramp was described, herein.

Comparison of Application Examples 2 and 3

The soft stop used in application example 2 is in contrast to the hard stop used in application example 3, which consists of a material that substantially does not allow any deformation or compression under manually applied force, and thus substantially also does not allow any additional advance. In exemplary embodiment 3, a so-called hard stop is combined with a ramp. If the ramp and hard stop are matched with each another in such a way that the hard stop can be pushed with increased force with increasing deformation against the ramp, this also results in a reserve feed which can be used to eject the lens for good with additional force if the piston rod is too short.

While specific embodiments have been described above, it is obvious that different combinations of the possible embodiments shown can be used, provided that the possible embodiments are not mutually exclusive.

While the invention has been described above with reference to specific embodiments, it is obvious that changes, modifications, variations and combinations can be made without departing from the spirit of the invention.

The invention claimed is:

1. An injector comprising:

an elongate injector body with a piston passage within which an injector piston rod having a screw thread is guided in a longitudinally displaceable manner, wherein the injector is provided with two operating modes for the displacement of the injector piston rod, and is able to be switched between the two operating modes, wherein a first operating mode defines an ejection operation and a second operating mode defines a screwing operation, wherein the injector body has at least one retractable and deployable wing grip, wherein the first operating mode is set to ejection operation by a deployed position of the wing grip and the second operating mode is set to screwing operation by a retracted position of the wing grip.

2. The injector according to claim 1, wherein the at least one retractable and deployable wing grip can be deployed from a front with respect to the injector body and can be retracted towards the front with respect to the injector body.

3. The injector according to claim 1, wherein the injector body has at least one displaceable thread web configured to be pushed in and out.

4. The injector according to claim 3, wherein the thread web is pushed out of the piston passage when the wing grip is deployed and pushed into the piston passage when the wing grip is retracted.

5. The injector according to claim 3, wherein the at least one wing grip and the at least one thread web are arranged in operative connection in such a way that by retracting the at least one wing grip the at least one thread web can be guided into a first position in which the at least one thread web forms a mating thread for the screw thread of the injector piston rod and by deploying the at least one wing grip the at least one thread web can be guided into a second position in which the at least one thread web does not form a mating thread for the screw thread of the injector piston rod.

6. The injector according to claim 3, wherein the wing grip and the thread web are in operative connection with one another in such a way that when the wing grip is retracted, the wing grip cannot be deployed by mechanical pressure of the piston rod on the thread web as it arises when screwing in the piston rod.

7. The injector according to claim 3, wherein the wing grip and the thread web are in operative connection with one another in such a way that when the wing grip is retracted, the wing grip also remains in the retracted position when, during screwing in the piston rod, the piston rod exerts mechanical pressure on the thread web.

8. The injector according to claim 3, wherein the at least one retractable and deployable wing grip has an axis of rotation about which the wing grip is retractable and deployable.

9. The injector according to claim 8, wherein the wing grip and the thread web are in operative connection with one another via a pressure means which, on the wing grip, is formed in an eccentric manner with respect to the axis of rotation of the wing grip.

10. The injector according to claim 9, wherein the pressure means holds the thread web in a first position when the wing grip is retracted, in which position the at least one thread web forms a mating thread for the screw thread of the injector piston rod so that the injector piston rod can be screwed, and the pressure means holds the thread web in a second position when the wing grip is deployed, in which position the at least one thread web does not form a mating thread for the screw thread of the injector piston rod, so that the injector piston rod can be pushed.

11. The injector according to claim 3, wherein the at least one thread web is formed on at least one movable holder which is movable in such a manner that the distance between the thread web to the piston passage can be changed by adjusting the wing grip position.

12. The injector according to claim 11, wherein the at least one movable holder is designed as a fork with an inner leg and an outer leg, wherein the inner and outer legs comprise the pressure means.

13. The injector according to claim 3, wherein, for the purpose of dual injection function, the at least one wing grip and the at least one thread web are cooperatively connected to one another, so that when retracting or pushing in the at least one wing grip the at least one thread web is guided from the ejection mode to the screwing mode (i.e., an active position in which the thread web cooperates with the screw thread of the injector piston rod.

14. The injector according to claim 3, wherein, for the purpose of dual injection function, the injector body is designed in such a way that the injector functions as an ejection injector or as a screw injector depending on the position of the at least one wing grip and/or of the at least one thread web.

15. The injector according to claim 1, wherein the at least one retractable and deployable wing grip is attached to the injector body along its length in a retractable and deployable manner.

16. The injector according to claim 1, wherein the at least one retractable and deployable wing grip is designed as a double wing grip, with a first wing and a second wing, the first wing and the second wing attached opposite one another along a length of the injector body in a retractable and deployable manner.

17. The injector according to claim 16, wherein retracting and deploying movement of first and second wings are synchronized, e.g., via a toothing.

18. The injector according to claim 1, wherein the injector piston rod is designed at a rear with an actuating element for manual operation of the piston.

19. The injector according to claim 1, wherein the at least one wing grip is configured so that the retracting and deploying of the wing grip can be repeated.

20. The injector according to claim 1, wherein the injector piston rod.

21. The injector according to the preceding claim 20, wherein the stop element is a displaceable stop element.

22. The injector according to claim 20, wherein the stop element is configured as a compressible stop element.

23. The injector claim 20, wherein the stop element is made from an elastic material.

24. The injector according to claim 20, wherein the injector piston rod is designed at a rear with an actuating element used as the actuating element for manual operation of the piston and as retention for the stop element.

25. The injector according to claim 1, wherein the injector is configured for injecting an intraocular lens into an eye or for implanting a corneal endothelial tissue into an eye.

* * * * *